(12) United States Patent
Broughton et al.

(10) Patent No.: US 6,395,766 B1
(45) Date of Patent: May 28, 2002

(54) TETRAHYDROINDOLONE DERIVATIVES AS GABAAALPHA5 LIGANDS FOR ENHANCING COGNITION

(75) Inventors: Howard Barff Broughton, Bishops Stortford; Helen Jane Bryant, Roydon; Mark Stuart Chambers, Puckeridge; Neil Roy Curtis, Buntingford, all of (GB)

(73) Assignee: Merck Sharp & Dohme Limited, Hoddesdon (GB)

(*) Notice: Subject to any disclaimer, the term of this patent is extended or adjusted under 35 U.S.C. 154(b) by 0 days.

(21) Appl. No.: 09/674,740

(22) PCT Filed: Jun. 2, 1999

(86) PCT No.: PCT/GB99/01799

§ 371 (c)(1),
(2), (4) Date: Nov. 6, 2000

(87) PCT Pub. No.: WO99/62899

PCT Pub. Date: Dec. 9, 1999

(30) Foreign Application Priority Data

Jun. 4, 1998 (GB) ............................................. 9812038

(51) Int. Cl.[7] .................. A61K 31/404; A61K 31/4439; A61P 25/00; C07D 209/08; C07D 209/30
(52) U.S. Cl. ....................... 514/411; 514/412; 548/427; 548/450; 548/466; 548/467; 548/512; 548/516
(58) Field of Search ................................. 548/516, 512, 548/466, 467, 450, 427; 514/412, 411

(56) References Cited

U.S. PATENT DOCUMENTS 5,723,462 A    3/1998   Albaugh et al. ............ 514/249

FOREIGN PATENT DOCUMENTS

| GB | 1150397 | 2/1968 |
|---|---|---|
| WO | WO95/11885 | 5/1995 |
| WO | WO96/16954 | 6/1996 |
| WO | WO97/26243 | 7/1997 |
| WO | WO97/34870 | 9/1997 |
| WO | WO98/02420 | 1/1998 |
| WO | WO98/02433 | 1/1998 |
| WO | WO98/18792 | 5/1998 |

OTHER PUBLICATIONS

Van Rhee et al. J. Med. Chem. 39: 398–406 (1996).
B.G. McDonald et al. J. Chem. Soc. 15: 1446–1450 (1975).

Primary Examiner—Mark L Berch
Assistant Examiner—Al Kahsay Habte
(74) Attorney, Agent, or Firm—J. Eric Thies; Shu Muk Lee; David L. Rose

(57) ABSTRACT

Compounds according to Formula (I) or a pharmaceutically acceptable salt thereof are GABA-A Alpha 5 ligands useful for enhancing cognition:

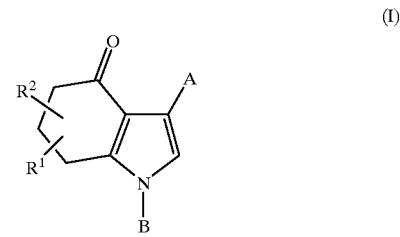

where A is $C_{1-6}$alkyl, $C_{2-6}$alkenyl, $C_{2-6}$alkynyl, $C_{3-6}$cycloalkyl, aryl$C_{1-6}$alkyl, or aryl wherein the aryl group is optionally substituted by halogen, $C_{1-6}$alkyl, $CF_3$, CN, $NO_2$ or $NH_2$, $NR^1R_{10}$, $S(O)_pR^1$, heteroaryl$C_{1-6}$alkyl or heteroaryl where heteroaryl is a 5- or 6-membered heteroaromatic ring as defined for B; and B is phenyl or a 5-membered ring having one or two unsaturations containing 1, 2, 3, or 4 heteroatoms chosen from O, N and S provided that not more than one heteroatom is other than N, a 6-membered heteroaromatic ring containing 1, 2, 3 or 4 nitrogen atoms, each of which rings is optionally substituted by one or more substituents.

7 Claims, No Drawings

TETRAHYDROINDOLONE DERIVATIVES AS GABAAALPHA5 LIGANDS FOR ENHANCING COGNITION

This is an application under 35 U.S.C. 371 of PCT/GB99/01799 and claims priority from Great Britain Application No. 9812038.9, filed Jun. 4, 1998.

BACKGROUND

The present invention relates to tetrahydroindolone derivatives, pharmaceutical compositions comprising them and to their use in therapy. More particularly, this invention is concerned with substituted derivatives which are ligands for $GABA_A$ receptors, in particular for $GABA_A$ α5 receptors and are therefore useful in therapy particularly where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, α β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agoilists or antagonists were known.

It is now believed that agents acting as BZ agonists at α1βγ2, α2βγ2 or α3βγ2 subunits will possess desirable anxiolytic properties. The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which bind more effectively to the α2 and/or α3 subunit than to al will be effective in the treatment of anxiety with a reduced propensity to cause sedation. Also, agents which are antagonists or inverse agonists at α1 might be employed to reverse sedation or hypnosis caused by α1 agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the $GABA_A$ α5 receptor subtype.

WO-A-9616954 mentions three thienylcyclohexanone derivatives in substituted by substituted arylaminocarbonyl on the thiophene ring as fungicides.

Van Rhee et al, *J. Med. Chem.*, 1996, 39, 398–406 discloses related compounds as adenosine receptor antagonists which differ in having an ester group on the thiophene ring.

SUMMARY OF THE INVENTION

The present invention is directed to compounds according to Formula (I) or a pharmaceutically acceptable salt thereof that are GABA-A Alpha 5 ligands useful for enhancing cognition:

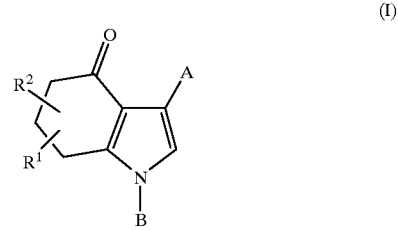

DETAILED DESCRIPTION OF THE INVENTION

The present invention provides a compound of formula (I) or a pharmaceutically acceptable salt thereof.

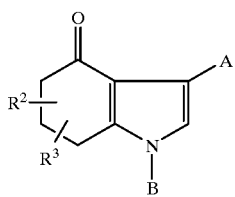

(I)

where A is $C_{1-6}$alkyl, $C_{2-6}$alkenyl, $C_{2-6}$alkynyl, $C_{3-6}$cycloalkyl, aryl$C_{1-6}$alkyl, or aryl wherein the aryl group is optionally substituted by halogen, $C_{1-6}$alkyl, $CF_3$, CN, $NO_2$ or $NH_2$, $NR^1R^{10}$, $S(O)_pR^1$, heteroaryl$C_{1-6}$alkyl or heteroaryl where heteroaryl is a 5- or 6-membered heteroaromatic ring as defined for B below;

B is phenyl or a 5-membered ring having one or two unsaturations containing 1, 2, 3 or 4 heteroatoms chosen from O, N and S provided that not more than one heteroatom is other than N, a 6-membered heteroaromatic ring containing 1, 2, 3 or 4 nitrogen atoms, each of which rings is optionally substituted by one or more substituents independently chosen from: cyano; $C_{1-6}$alkyl; $C_{1-6}$haloalkyl; halogen; $S(O)_rR^4$; $COR^5$; and aryl, aryl$C_{1-6}$alkyl or a 5-membered ring having one or two unsaturations containing 1, 2, 3 or 4 heteroatoms chosen from O, N and S provided that not more than one heteroatom is other than N wherein the aryl ring or 5-membered ring is optionally substituted by one, two or three substituents independently chosen from halogen, $CF_3$, $OCH_3$, nitro and cyano; and when a nitrogen ring atom is present it is optionally substituted by oxygen;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$ cycloalkyl group;

$R^4$ is hydrogen, $C_{1-8}$alkyl, $C_{2-8}$alkenyl, $C_{2-8}$alkynyl, aryl or $CH_2(CO)_mNR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{10}$ is hydrogen or $C_{1-6}$ alkyl;

$R^{14}$ is hydrogen or $C_{1-6}$alkyl;

m is zero or 1;

p is zero, 1 or 2;

q is 1 or 2;

r is 0, 1 or 2;

s is 0, 1 or 2; and t is 0, 1 or 2.

B may be phenyl or a 5-membered ring having one or two unsaturations containing 1, 2, 3 or 4 heteroatoms chosen from O, N and S provided that not more than one heteroatom is other than N, or a 6-membered aromatic ring containing 1, 2, 3 or 4 nitrogen atoms, which ring is optionally substituted by one or more substituents independently chosen from: $C_{1-6}$alkyl; $C_{1-6}$haloalkyl; halogen; $S(O)_rR^4$; $COR^5$; and aryl or aryl$C_{1-6}$alkyl wherein the aryl ring is optionally substituted by one, two or three substituents independently chosen from halogen, $CF_3$, $OCH_3$, nitro and cyano; and when a nitrogen ring atom is present it is optionally substituted by oxygen.

B is preferably an optionally substituted phenyl or optionally substituted 6-membered heteroaromatic ring. The optional substituents are preferably one or two groups independently chosen from halogen, $C_{1-6}$alkyl, trifluoromethyl, cyano and an unsubstituted 5-membered heteroaromatic ring containing 1, 2, 3 or 4 heteroatoms chosen from O, N and S in which not more than one heteroatom is other than N. The optional substituent is preferably chosen from halogen, $C_{1-6}$alkyl, trifluoromethyl and cyano.

B is most particularly optionally substituted phenyl or pyridine. In particular B may be pyridine and preferably pyridin-2-yl.

Thus when B is a heteroaromatic ring it may be a thiazole, pyrazole, pyrimidine, tetrazole, triazole, oxadiazole, oxazole, pyridine, imidazole or pyrazine which is unsubstituted or substituted by $C_{1-6}$alkyl, halogen, $SR^4$, $COR^5$ or benzyl optionally substituted by halogen. When B is a 5- or 6-membered ring having one unsaturation it is preferably oxazolidinyl or imidazolinyl optionally substituted by halogen or $C_{1-4}$alkyl.

Particular embodiments of B are (1-phenylsulphonyl)pyrazol-3-yl, 1-acetylpyrazol-3-yl, (3-ethoxycarbonyl)isoxazol-5-yl, (3-isopropyl)-1,2,4-oxadiazol-5-yl, imidazolin-2-yl, pyrazol-4-yl, 2-methyl-1,3,4-oxadiazol-5-yl, oxazolidin-2-yl, 2-methyltetrazol-5-yl, pyrazol-3-yl, 2-propyltetrazol-5-yl, thiazol-2-yl, 4-methyl-1,2,4-triazol-3-yl, (4-ethoxycarbonyl)thiazol-2-yl, (4-trifluoromethyl)thiazol-2-yl, (4-acetyl)thiazol-2-yl, (4-methyl)thiazol-2-yl, pyrrol-2-yl, pyrid-2-yl, 3-methyl-1,2,4-oxadiazol-5-yl, 4-benzyl-1,2,4-triazol-3-yl, 1-methyl-1,2,4-triazol-3-yl, oxazol-2-yl, pyrazin-2-yl, pyrimidin-5-yl, 3-(N-methylaminocarbonyl)thiazol-2-yl, thiazol-5-yl, isoxazol-5-yl, pyrid-3-yl, pyrid-4-yl, 1,3,4-oxadiazol-5-yl and 1-methylsulphonylpyrazol-3-yl.

Other particular embodiments of B are pyridin-2-yl, 6-methyl pyridin-2-yl, thiazol-2-yl, 4-chlorophenyl, 4-fluorophenyl, 3-fluorophenyl, 4-trifluoromethylphenyl, 4-methylphenyl, 3-methylphenyl, pyrimidin-2-yl, pyridin-3-yl, 2-cyanophenyl, 5-chloropyridin-2-yl and 6-(thiazol-2-yl)pyridin-2-yl.

$R^1$ is preferably $C_{1-6}$alkyl, $C_{2-6}$alkenyl or $C_{3-6}$cycloalkyl each of which is optionally substituted by amino, di($C_{1-6}$alkyl)amino, hydroxy, $C_{1-6}$alkoxy, $C_{1-6}$alkylaminocarbonyl or one, two or three halogen atoms; aryl or aryl$_{1-6}$alkyl optionally substituted on the aryl ring by halogen, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, which ring is optionally substituted by halogen, $C_{1-6}$alkoxy, $C_{1-6}$alkylthio, aryl or $C_{1-6}$alkyl.

More preferably $R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio. In particular $R^1$ is $C_{1-6}$alkyl, phenyl, benzyl or pyridyl.

A may be $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, heteroaryl$C_{1-6}$alkyl or heteroaryl where heteroaryl is a 5-membered ring having one or two unsaturations containing 1, 2, 3 or 4 heteroatoms chosen from O, N and S provided that not more than one heteroatom is other than N, or a 6-membered aromatic ring containing 1, 2, 3 or 4 nitrogen atoms, which ring is optionally substituted by one or more substituents independently chosen from: $C_{1-6}$alkyl; $C_{1-6}$haloalkyl; halogen; $S(O)_rR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano; and when a nitrogen ring atom is present it is optionally substituted by oxygen.

When A is not $S(O)_pR^1$ it is preferably $C_{1-6}$alkyl, $C_{2-6}$alkenyl or $C_{3-6}$cycloalkyl. A may be $C_{1-6}$alkyl such as ethyl.

A is preferably $C_{1-6}$alkyl, $C_{2-6}$alkenyl, aryl$C_{1-6}$alkyl or aryl wherein the aryl group is optionally substituted by a halogen atom or a $C_{1-6}$alkyl group, a 5- or 6-membered heteroaromatic ring optionally substituted by a halogen atom or $C_{1-6}$alkyl, $NHR^1$ or $SR^1$.

Particular embodiments of A include ethyl, 1,1-dimethylethyl, cyclopropyl, thiazol-2-yl, ethylthio, benzyl, phenyl, methylthio, ethenyl, phenylamino, pyridin-2-ylamino, phenylthio, pyrid-2-yl, benzylthio, oxazol-2-yl, 3-methyl-1,2,4-oxadiazol-5-yl, thiazol-5-yl, 4-chlorophenyl, 4-methylthiazol-2-yl, 3-chlorophenyl and 2-chlorophenyl.

Particular embodiments of A are phenyl, cyclohexyl, 2-methylprop-1-enyl, methylthio, ethyl, isopropyl, propyl, cyclobutyl, but-3-enyl, cyclopropyl, methanesulphonyl, methyl, benzyl, methanesulphinyl, (1,1-dimethylethyl)thio, pentylthio, (4-methyl-1,2,4-triazol-3-yl)thio, hexylthio, benzylamino, (3-imidazol-1-ylpropyl)amino, (pyrid-2-yl)amino, 2-methylprop-1-yl, [3-(4-methylpiperazin-1-yl)propyl]amino, methylamino, (2-hydroxyethyl)amino, azetidin-1-yl, tert-butylamino, isopropylthio, (2-hydroxyethyl)thio, methoxy, dimethylamino, cyclobutoxy, phenoxy, butylthio, (3-chloropropyl)thio, (2-phenylethyl)thio, propylthio, (2-methylbutyl)thio, (2,2,2-trifluoroethyl)thio, (1-methylpropyl)thio, (4-chlorophenyl)thio, (3-fluorophenyl)thio, (4-acetylaminophenyl)thio, (4-methoxyphenyl)thio, (1-methylimidazol-2-yl)thio, (thiophen-2-yl)thio, (imidazol-2-yl)thio, (4-phenylthiazol-2-yl)thio, (1,2,4-triazol-3-yl)thio, (5-methyl-1,3,4-thiadiazol-2-yl)thio, (5-methylthio-1,3,4-thiadiazol-2-yl)thio, benzylthio, cyclopentylthio, (2-methylpropyl)thio, (furan-2-ylmethyl)thio, (2-hydroxy-1-methylpropyl)thio, (2,3-dihydroxypropyl)thio, (2-hydroxypropyl)thio, ((N-methylaminocarbonyl)methyl)thio, (pyrid-4-yl)thio, (pyrimidin-2-yl)thio, (thiazol-2-yl)thio, prop-2-enylthio, (pyrid-2-yl)thio, ethylthio, phenylthio, (N,N-dimethyl-2-aminoethyl)thio, (2-methoxyethyl)thio, (furan-2-ylmethyl)amino, (2-methylpropyl)amino, propylamino, (2-methoxyethyl)amino, cyclopropylamino, isopropylamino, ethylamino, cyclobutylamino and isopropoxy.

When A is heteroaryl it may be a thiazole, pyrazole, pyrimidine, tetrazole, triazole, oxadiazole, oxazole, pyridine, imidazole or pyrazine.

$R^2$ and $R^3$ are preferably independently chosen from hydrogen, methyl and propyl or are attached to the same carbon atom and together with that atom form a $C_{3-6}$cycloalkyl group. Alternatively $R^2$ and $R^3$ are independently chosen from hydrogen and methyl. $R^2$ may be hydrogen with $R^3$ being hydrogen, methyl or isopropyl. Preferably both are methyl. Preferably $R^2$ and $R^3$ are geminal to each other, preferably at the 6-position, i.e. beta to the carbonyl group in formula I.

$R^4$ may by hydrogen, $C_{1-4}$alkyl, $C_{2-4}$alkenyl, $C_{2-4}$alkynyl, aryl or $CH_2(CO)_mNR^8R^9$. $R^4$ is preferably hydrogen, $C_{1-4}$alkyl or $CH_2(CO)_mNR^8R^9$, more preferably hydrogen, methyl or $CH_2CONR^8R^9$ and most preferably methyl or $CH_2CONR^8R^9$.

$R^5$ is preferably methyl, methoxy, ethoxy or $NR^6R^7$ and most preferably methyl, ethoxy or $NR^6R^7$.

$R^6$ may be hydrogen, $C_{1-4}$alkyl, $C_{2-4}$alkenyl, $C_{2-4}$alkynyl, aryl or $CH_2(CO)_mNR^8R^9$. $R^6$ is preferably hydrogen or $C_{1-4}$alkyl and most preferably hydrogen.

$R^7$ is preferably phenyl unsubstituted or substituted by halogen, nitro or cyano, more preferably optionally substituted by halogen, such as chlorine.

$R^8$ is preferably hydrogen or $C_{1-6}$alkyl and most preferably hydrogen.

$R^9$ is preferably $C_{1-6}$alkyl or phenyl unsubstituted or substituted by one, two or three substituents independently chosen from halogen, nitro and cyano, more preferably $C_{1-6}$alkyl or phenyl optionally substituted by one or two substituents independently chosen from halogen and nitro and most preferably tert-butyl or phenyl optionally substituted with one or two substituents chosen from chlorine and nitro, such as 4-chlorophenyl.

$R^{10}$ is preferably hydrogen or methyl, particularly hydrogen.

$R^{14}$ is generally hydrogen or $C_{1-4}$alkyl and most preferably hydrogen.

m is preferably 1.
p is preferably zero or two, most preferably zero.
q is preferably 1.
r is preferably 1.
s is preferably 0 or 1. s may be 1. s may be 0.
t is preferably 0 or 1. t may be 1. t may be 0.

A specific Example of a compound according to the present invention is:

6,6-dimethyl 3-ethyl-1-(pyridin-2-yl)-4,5,6,7-tetrahydroindol-4-one and the pharmaceutically acceptable salts thereof.

Further specific Examples of compounds according to the present invention are:

6,6-dimethyl-3-(1,1-dimethylethyl)-1-(pyridin-2-yl)-4,5,6,7-tetrahydroindol-4-one;

3-cyclopropyl-6,6-dimethyl-1-pyridin-2-yl)-4,5,6,7-tetrahydroindol-4-one;

3-ethyl-6,6-dimethyl-1-(pyrimidin-2-yl)-4,5,6,7-tetrahydroindol-4-one;

6,6-dimethyl-3-ethyl-1-(thiazol-2-yl)-4,5,6,7-tetrahydroindol-4-one;

6,6-dimethyl-3-ethyl-1-(3-fluorophenyl)-4,5,6,7-tetrahydroindol-4-one;

6,6-dimethyl-3-ethyl-1-(4-trifluoromethylphenyl)-4,5,6,7-tetrahydroindol-4-one;

6,6-dimethyl-3-ethyl-1-(4-methylphenyl)-4,5,6,7-tetrahydroindol-4-one;

1-(4-chlorophenyl)-6,6-dimethyl-3-ethyl-4,5,6,7-tetrahydroindol-4-one;

6,6-dimethyl-3-ethyl-1-(4-fluorophenyl)-4,5,6,7-tetrahydroindol-4-one;

6,6-dimethyl-3-ethyl-1-(3-methylphenyl)-4,5,6,7-tetrahydroindol-4-one;

6,6-dimethyl-3-methylthio-1-(pyridin-2-y1)-4,5,6,7-tetrahydroindol-4-one;

6,6-dimethyl-3-ethylthio-1-(pyridin-2-yl)-4,5,6,7-tetrahydroindol-4-one;

6,6-dimethyl-3(phenylmethyl)thio-1-(pyridin-2-yl)-4,5,6,7-tetrahydroindol-4-one;

6,6-dimethyl-1-pyridin-2-yl)-3-(thiazol-2-yl)-4,5,6,7-tetrahydroindol-4-one;

6,6-dimethyl-3-phenyl-1-(pyridin-2-yl)-4,5,6,7-tetrahydroindol-4-one;

6,6-dimethyl-1-(pyridin-2-yl)-3-pyridin-2-yl)-4,5,6,7-tetrahydroindol-4-one;

6,6-dimethyl-1-(pyridin-2-yl)-3-vinyl-4,5,6,7-tetrahydroindol-4-one;

6,6-dimethyl-3-phenylmethyl-1-(pyridin-2-yl)-4,5,6,7-tetrahydroindol-4-one;

6,6-dimethyl-3-(oxazol-2-yl)-1-(pyridin-2-yl)-4,5,6,7-tetrahydroindol-4-one;

6,6-dimethyl-1-(pyridin-2-yl)-3-(thiazol-5-yl)-4,5,6,7-tetrahydroindol-4-one;

6,6-dimethyl-3-phenylamino-1-(pyridin-2-yl)-4,5,6,7-tetrahydroindol-4-one;

6,6-dimethyl-1-(pyridin-2-yl)-3-(pyridin-2-ylamino)-4,5,6,7-tetrahydroindol-4-one;

6,6-dimethyl-3-ethyl-1-(6-methylpyridin-2-yl)-4,5,6,7-tetrahydroindol-4-one;

6,6-dimethyl-3-(4-methylthiazol-5-yl)-1-(pyridin-2-yl)-4,5,6,7-tetrahydroindol-4-one;

3-(4-chlorophenyl)-6,6-dimethyl-1-(pyridin-2-yl)-4,5,6,7-tetrahydroindol-4-one;

3-(3-chlorophenyl)-6,6-dimethyl-1-(pyridin-2-yl)-4,5,6,7-tetrahydroindol-4-one;

3-(2-chlorophenyl)-6,6-dimethyl-1-(pyridin-2-yl)-4,5,6,7-tetrahydroindol-4-one;

6,6-dimethyl-1-(pyridin-3-yl)-3-(thiazol-2-yl)-4,5,6,7-tetrahydroindol-4-one;

1-(5-chloropyridin-2-yl)-6,6-dimethyl-3-(thiazol-2-yl)-4,5,6,7-tetrahydroindol-4-one;

6,6-dimethyl-3-(thiazol-2-yl)-1-(6-(thiazol-2-yl)pyridin-2-yl)-4,5,6,7-tetrahydroindol-4-one;

1-(2-cyanophenyl)-6,6-dimethyl-3-(thiazol-2-yl)-4,5,6,7-tetrahydroindol-4-one; and the pharmaceutically acceptable salts thereof.

Further specific compounds of the present invention are:

6,6-dimethyl-3-ethyl-1-(6-methylpyridin-2-yl)-4,5,6,7-tetrahydroindol-4-one;

6,6-dimethyl-3-(3-methyl-1,2,4-oxadiazol-5-yl)-1-(pyridin-2-yl)-4,5,6,7-tetrahydroindol-4-one;

6,6-dimethyl-3-(3-methylthiazol-5-yl)-1-(pyridin-2-yl)-4,5,6,7-tetrahydroindol-4-one;

3-(1,1-dimethylethyl)-6-methyl-1-(pyridin-2-yl)-4,5,6,7-tetrahydroindol-4-one;

3-ethyl-6-methyl-1-(pyridin-2-yl)-4,5,6,7-tetrahydroindol-4-one;

6-methyl-1-(pyridin-2-yl)-3-(thiazol-2-yl)-4,5,6,7-tetrahydroindol-4-one;

3-(1,1-dimethylethyl)-6-(2-methylethyl)-1-(pyridin-2-yl)-4,5,6,7-tetrahydroindol-4-one 1-(pyridin-2-yl)-3-(thiazol-2-yl)-4,5,6,7-tetrahydroindol-4-one; and the pharmaceutically acceptable salts thereof.

There is also provided a pharmaceutical composition comprising a compound of formula I according to the present invention, or a pharmaceutically acceptable salt thereof, and a pharmaceutically acceptable excipient.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the $\alpha$5 subunit. In particular, they are desirably inverse agonists of the $\alpha$5 subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $\alpha$2 or $\alpha$3 subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha$5 subunit, in particular for conditions requiring cognition enhancement such as Alzheimer's disease. Other conditions to be treated include cognition deficits due to traumatic injury, stroke, Parkinson's disease, Downs syndrome, age related memory deficits, attention deficit disorder and the like.

There is also disclosed a method of treatment or prevention of a condition associated with $GABA_A$ receptors containing the $\alpha$5 subunit in a subject suffering from or prone to such a condition which comprises administering to that subject a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "$C_{1-4}$alkyl", "$C_{2-4}$alkenyl" and "$C_{2-4}$alkynyl" are to be construed in an analogous manner.

The expression "$C_{3-6}$cycloalkyl" includes cyclopropyl, cyclobutyl, cyclopentyl and cyclohexyl groups. "$C_{5-6}$cycloalkenyl", "$C_{3-8}$cycloalkyl" and "$C_{5-7}$cycloalkyl" are to be construed analogously.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine, especially fluorine, chlorine and bromine.

The expression "aryl$C_{1-6}$alkyl" as used herein includes benzyl, phenylethyl, phenylpropyl and naphthylmethyl. "Aryl$C_{2-6}$alkenyl", "aryl$C_{2-6}$alkynyl" and "heteroaryl$C_{1-6}$alkyl" should be construed in an analogous fashion.

Typical aryl groups include phenyl and naphthyl. Preferably the aryl is phenyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a process for producing a compound of formula I which comprises reacting a compound of formula II with a compound of formula III:

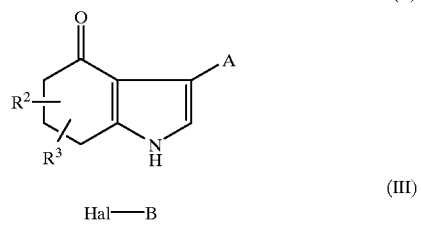

(II)

Hal—B (III)

wherein $R^2$, $R^3$, A and B are as defined above and Hal is a halogen atom such as bromine, chlorine or fluorine, generally in a solvent such as DMF and in the presence of a strong base such as NaH, generally with heating to about 90° C. for about 6 h. Alternatively the reaction may be carried out using CuBr in DMF in the presence of $K_2CO_3$ generally with heating to about 180° C. for about 48 h.

The compound of formula II is prepared by decarboxylating a compound of formula IV:

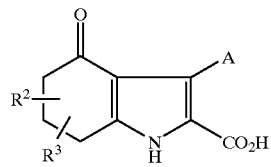

(IV)

wherein $R^2$ and $R^3$ are as defined above by heating at about 100° C. for about 45 minutes generally in the presence of an acid such as acetic acid and/or hydrochloric acid.

The compounds of formula IV is prepared by hydrolysing a compound of formula V:

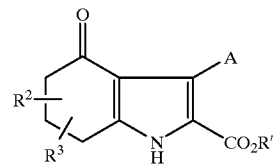

(V)

wherein $R^2$ and $R^3$ are as defined above generally by heating at reflux for about 6 h generally in the presence of a base such as KOH and a solvent such as ethanol and water. This reaction can also be performed by heating the compound of formula V in DMSO and $H_2O$ at about 150° C. for about 18 h.

The compound of formula V is prepared by reacting a compound of formula VI with a compound formula VII:

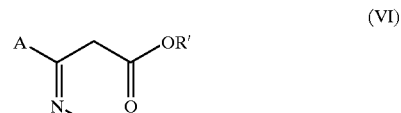

(VI)

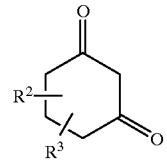

(VII)

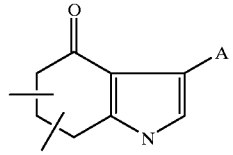

wherein A and $R^1$ are defined above, generally with heating to about 100° C. for about 1 h in a buffered solution such as acetic acid/sodium acetate in the presence of a catalyst such as zinc optionally in powdered form. This reaction can produce a compound of formula II directly when it is carried out at 150° C.

The compound of formula VI is prepared by reacting a compound of formula VIII:

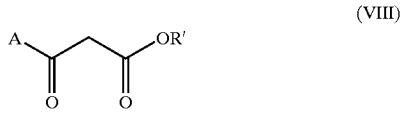

(VIII)

wherein A and R' are as defined above, with sodium nitrite generally in the presence of an acid such as acetic acid in a solvent such as water at room temperature for about 1 h.

The compounds of formulae III, VII and VIII are either commercially available or can be made by the skilled person from commercially available compounds by known methods.

In an alternative process, a compound of formula II in which A is $SR^1$, wherein $R^1$ is as defined above, is prepared by reacting a compound of formula IX:

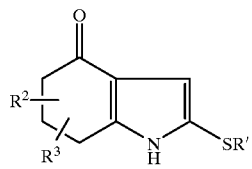

(IX)

wherein $R^2$ and $R^3$ are as defined above, with heating for about four hours in the presence of an acid such as trifluoroacetic acid, generally in a solvent such as $ClCH_2CH_2Cl$. The resulting product is a mixture of compounds of formulae II and IX which are then separated by conventional means.

The compound of formula IX is prepared by reacting a compound of formula X:

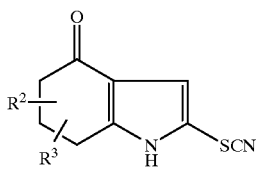

(X)

wherein $R^2$ and $R^3$ are as defined above, with $R^1I$, wherein $R^1$ is as defined above, in the presence of a solvent such as methanol with a base as ROH for about 3 h at room temperature. The compound $R^1I$ is commercially available or may be made by methods known to the skilled person from commercially available compounds.

The compound of formula X is made by reacting a compound of formula XI:

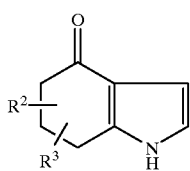

(XI)

wherein $R^2$ and $R^3$ are as defined above, with bromine and KSCN in a solvent such as methanol at a temperature of from –30° C. to room temperature.

The compound of formula XI can be made by reacting a compound of formula VII with a compound of formula XII:

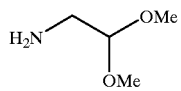

(XII)

with paratoluensulphonic acid generally in a solvent such as toluene with heating for about 3 h, and then carrying out a Michael addition by heating at about 40° C. for about 9 h with an acid such as HCl, preferably at 3N.

The compound of formula XII is commercially available or can be made by known methods from commercially available compounds.

Alternatively the compound of formula XI may be obtained commercially.

Alternatively a compound of formula I is produced by reacting a compound of formula XIII with a compound of formula XIV:

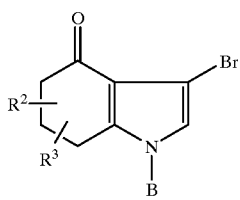

(XIII)

(XIV)

wherein $R^2$, $R^3$, A and B are as defined above:

(i) where Z is $Sn(Bu)_3$ in the presence of tetrakis (triphenylphosphene) palladium or dichlorobis (triphenylphosphine) palladium in a solvent such as dioxan generally with heating to reflux in a solvent such as dioxan or hexamethylphosphoramide for about 24 h to 48 h at about 70° C.;

(ii) where Z is $B(OH)_2$ in the presence of tetrakis (triphenylphosphene) palladium generally in a biphasic mixture of solvents such as ethylene glycol dimethyl ether and water and in the presence of a mild base such as $Cs_2CO_3$ or $Na_2CO_3$ at reflux for about 8 h; or in the presence of $Cu(OAc)_2$ in a solvent such as DCM, in the presence of a base such as $Et_3N$ generally at room temperature;

(iii) where Z is $NR^{10}H$ in the presence of tris (dibenzylideneacetone)dipalladium generally with a base such as $NaO^tBu$, a solvent such as toluene and a compound such as (R)-(+)-2,2'-bis (diphenylphosphino)-1,1-binaphthyl generally at reflux for about 3 h. (This last method produces compounds of formula I in which A is $NR^1R^{10}$).

The compound of formula XIII can be produced by reacting a compound of formula XV:

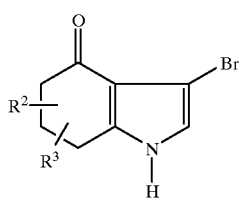

(XV)

wherein $R^2$ and $R^3$ are as defined above with a compound of formula III as defined above generally in the presence of a strong base such as NaH and in a solvent such as DMF for about 5 min.

The compound of formula XV can be produced by reacting a compound of formula XVI:

(XVI)

[Structure: compound with R² and R³ substituents on a bicyclic ring with ketone (=O) and N-Si(iPr)₃ group]

wherein $R^2$ and $R^3$ are as defined above with a brominating agent such as N-bromosuccinimide generally in a solvent such as THF generally with cooling to about −78° C. for about 1 h.

The compound of formula XVI can be produced by reacting a compound of formula XI as defined above with ($^i$Pr)$_3$SiCl generally in a solvent such as DMF at about 0° C. for about 1 h.

Compounds of formula XIV are commercially available or can be made by known by methods from commercially available compounds.

A compound of formula I may also be prepared by interconversion from another compound of formula I by known methods.

Compounds of formula I in which A is $S(O)_pR^1$ wherein p is one or two can be obtained by reacting a compound of formula I in which A is $S(O)pR^1$ in which p is zero or one and $R^1$ is as defined above with a stoichiometric quantity of mCPBA, generally in a solvent such as $CH_2Cl_2$: dioxan with cooling to about −78° C.

It will be understood that the above transformations of $S(O)_pR^1$ are illustrative and other standard techniques known to the skilled person may alternatively be used.

The following Examples illustrate pharmaceutical compositions according to the invention.

COMPOSITION EXAMPLE 1A

Tablets containing 1–25 mg of compound

|  | Amount mg | | |
|---|---|---|---|
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

COMPOSITION EXAMPLE 1B

Tablets containing 26–100 mg of compound

|  | Amount mg | | |
|---|---|---|---|
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

COMPOSITION EXAMPLE 2

| Parenteral injection | Amount |
|---|---|
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

COMPOSITION EXAMPLE 3

| Topical formulation | Amount |
|---|---|
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human GABA$_A$ receptors containing the α5 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells;. 10 nM for (α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2:1.8 nM; for α2β3γ2:1.8 nM; for α3β3γ2:1.0 nM; for α5β3γ2:1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillate. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [3H]Ro 15-1788 from the α5 subunit of the human GABA$_A$ receptor of 500 nM or less, preferably of 100 nM or less, and more particularly of 50 nM or less.

More preferably the compounds of the present invention are inverse agonists at the GABA$_A$ α5 subtype whilst being substantially antagonists at the α1, α2 and α3 subtypes. Details of how the effects at the various subtypes can be measured are given in WO-A-9625948.

Further, the present compounds preferably bind preferentially to the GABA$_A$ α5 subtype when compared with the α1, α2 and α3 subtypes. The preferential binding is preferably 5-fold, more preferably 10-fold and most preferably 20-fold.

INTERMEDIATE 1

6,6-Dimethyl 3-ethyl-4,5,6,7-tetrahydro-1H-indol-4-one

Step 1: Ethyl 6,6-dimethyl 3-ethyl-4-oxo-4,5,6,7-tetrahydro-1H-indole-2-carboxylate Ethyl propionylacetate (15 g, 0.1 mol) and acetic acid (40 mL) were cooled to 10° C., and a solution of sodium nitrite (10.4 g, 0.15 mol) in water (40 mL) was added dropwise to the stirred mixture maintaining the temperature below 20° C. After addition the mixture was warmed to room temperature and stirred for 1 h. The mixture was then extracted with CH$_2$Cl$_2$ (3×100 mL) and washed with water (100 mL), NaHCO$_3$ (10% $^w$/v, 100 mL) and water (100 mL). The organic layer was separated dried (MgSO4) and evaporated to afford the oxime (13.2 g, 73%) as a yellow oil which solidified on standing. The oxime was used without further purification. $^1$H NMR (360 MHz, d$_6$-DMSO) δ 1.01 (3H,t, J=7.3 Hz), 1.23 (3H,t,J=7.1 Hz), 2.80 (2H,q,J=7.3 Hz), 4.24 (2H,q,J=7.1 Hz), 13.16 (1H,br s).

Sodium acetate trihydrate (7.8 g, 0.057 mol) and 5,5-dimethyl-1,3-cyclohexandione (10.7 g, 0.076 mol) in acetic acid (90 mL) were heated to 70° C. A solution of the oxime (13.2 g, 0.076 mol) in acetic acid (45 mL) was added portionwise whilst simultaneously adding zinc dust (8 g), over a period of 30 min, maintaining the temperature between 70–80° C. The solution was then heated at 100° C. for 1 h, cooled to 70° C., then water (20 mL) was added and heating continued at 100° C. for 6 h. The solution was then cooled to room temperature, poured into ice-water (400 mL) and extracted with CH$_2$Cl$_2$ (3×200 mL). The combined organic layers were washed with water (200 mL), separated, dried (MgSO$_4$) and evaporated. The residue was chromatographed on silica gel (hexane:EtOAc 4:1→1:1) and the fractions containing the desired product were combined and evaporated. The resultant orange solid was recrystallized from MeOH (30 ml) to afford the pyrrole (5.7 g, 28%) as a yellow solid. mp 163–166° C. $^1$H NMR (360 MHz, d$_6$-DMSO) δ 1.00 (6H,s), 1.06 (3H,t,J=7.3 Hz), 1.29 (3H,t, J=7.1 Hz), 2.23 (2H,s), 2.64 (2H,s), 2.98 (2H,q,J=7.3Hz), 4.25 (2H,q,J=7.1 Hz), 11.86 (1H,s). MS(ES$^+$) 264 (M+1). C$_{15}$H$_{21}$NO$_3$ requires: C, 68.42; H, 8.04; N, 5.32%. Found: C, 68.55; H, 8.12; N, 5.27%.

Step 2: 6,6-Dimethyl 3-ethyl-4-oxo-4,5,6,7-tetrahydro-1H-indole-2-carboxylic acid A solution of ethyl 6,6-dimethyl-3-ethyl-4-oxo-4,5,6,7-tetrahydro-1H-indole-2-carboxylate (5.4 g, 0.02 mol) and KOH (2.9 g, 0.05 mol) in EtOH (25 mL) and water (7.5 mL) was heated at reflux for 6 h. The mixture was cooled to 60° C., and neutralized by the addition of acetic acid. Water (80 mL) was added and the cream precipitate collected by filtration. The precipitate was washed with EtOH and hexane then dried under vacuum at 50° C. The acid (4 g, 83%) was isolated as a cream solid, and used without further purification. mp>198° C. $^1$H NMR (360 MHz, d$_6$-DMSO δ 1.00 (6H,s), 1.04 (3H,t,J=7.3 Hz), 2.22 (2H,s), 2.62 (2H,s), 2.98 (2H,q,J=7.3 Hz), 11.72 (1H, br s). C$_{13}$H$_{17}$NO$_3$. 0.4(H$_2$O) requires: C, 64.39; H, 7.40; N, 5.73%. Found:C, 64.38, H, 7.30; N, 5.70%. MS(ES$^+$) 236 (M+1).

Step 3: 6,6-Dimethyl-3-ethyl-4,5,6,7-tetrahydro-1H-indol-4-one

A suspension of 6,6-dimethyl-3-ethyl-4-oxo-4,5,6,7-tetrahydro-1H-indole-2-carboxylic acid (2.5 g, 0.011 mol) in acetic acid (12 mL) and hydrochloric acid (10M; 0.64 mL) was heated at 100° C. for 45 min. After this time water (50 mL) was added, the cooling bath removed and the solution stirred at room temperature for 2 h. The precipitate was collected by filtration and the title pyrrole (1.76 g, 87%) isolated as a colourless solid. mp. 150° C.–152° C. C$_{12}$H$_{17}$NO requires: C, 75.35; H, 8.96; N, 7.32%. Found: C, 75.00; H, 8.88; N, 7.24%. $^1$H NMR (250 MHz, CDCl$_3$) δ 1.10 (6H,s), 1.19 (3H,t,J=7.4 Hz), 2.32 (2H,s), 2.63 (2H,s), 2.75 (2H,d of q,J=7.4 and 1.0 Hz), 6.42 (1H,br s), 8.00 (1H,br s). MS (ES$^+$) 192 (M+1).

EXAMPLE 1

6,6-Dimethyl 3-Ethyl-1-(pyridin-2-yl)-4,5,6,7-tetrahydroindol-4-one

To a solution of 6,6-dimethyl 3-ethyl-4,5,6,7-tetrahydro-1H-indol-4-one (50 mg, 0.26 mmol) in DMF (4 mL) at 0° C., was added NaH (11 mg of a 60% dispersion in mineral oil, 0.29 mmol). The cooling bath was removed and the mixture stirred at room temperature for 20 min. After this time 2-fluoropyridine (26 μl, 0.29 mmol) was added and the residue heated at 90° C. for 6 h. The solvent was evaporated and the residue partitioned between EtOAc (20 mL) and water (20 mL). The organic layer was separated, dried (Na$_2$SO$_4$) and evaporated. The residue was chromatographed an silica gel, eluting with hexane:EtOAc (2:1), to give the title pyrrole (18 mg, 26%) as a colourless solid. mp 125–127° C. $^1$H NMR (360 MHz, CDCl$_3$) δ 1.10 (6H,s), 1.23 (3H,t,J=7.4 Hz), 2.38 (2H,s), 2.83 (2H,d of q, J=7.4 and 1.0 Hz), 2.92 (2H,s), 6.88 (1H,s), 7.25–7.27 (1H,m), 7.30 (1H,d,J=8.0 Hz), 7.82 (1H,d of t, J=7.7 and 1.9 Hz), 8.51–8.57 (1H,m). MS (ES$^+$) 269 (M+1).

EXAMPLE 2

6,6-Dimethyl-3-(1,1-dimethylethyl)-1-(pyridin-2-yl)-4,5,6,7-tetrahydroindol-4-one Step 1: 6,6-Dimethyl-3-(1,1-dimethylethyl)-4,5,6,7-tetrahydro-1H-indol-4-one Methyl 4,4-dimethyl-3-oxopentanoate (20 g, 0.13 mol) and AcOH (48 mL) were cooled to 10° C. and a solution of $NaNO_2$ (12.3 g, 0.19 mol) in water (48 mL) was added dropwise to the stirred mixture, maintaining the temperature below 20° C. After addition the mixture was warmed to room temperature and stirred for 2 h. The mixture was then extracted with DCM (3×100 mL). The combined organic layers were evaporated and the residue taken up in ether. The ethereal layer was washed with water (100 mL), separated and dried ($Na_2SO_4$). The resultant yellow gum (22.7 g, 96%) was used without further purification. $^1$H NMR (250 MHz, $CDCl_3$) δ 1.23 (9H,s), 3.89 (3H,s), 9.00–10.00 (1H,br s). Sodium acetate trihydrate (20.6 g, 0.15 mol) and 5,5-dimethyl-1,3-cyclohexandione (16.9 g, 0.12 mol) in propionic acid (140 mL) were heated to 150° C. A solution of the oxime (22.7 g, 0.12 mol) in propionic acid (70 mL) was added via a dropping funnel, whilst simultaneously adding zinc dust (12 g) over 20 min. The solution was heated at reflux for 24 h after which time it was poured into water. The resultant solid was collected by filtration then triturated with ether. The colourless solid (3.7 g, 14%) was collected by filtration. $^1$H NMR (360 MHz, $CDCl_3$) δ 1.10 (6H,s), 1.35 (9H,s), 2.35 (2H,s), 2.64 (2H,s), 6.43 (1H,d,J=2.2 Hz), 7.80–8.14 (1H,br s). MS (ES$^+$) 220 (M+1).

Step 2: 6,6-Dimethyl-3-(1,1-dimethylethyl)-1-(pyridin-2-yl)-4,5,6,7-1H-tetrahydroindol-4-one In the same was as described in Example 1 using 6,6-dimethyl-3-(1,1-dimethylethyl)-4,5,6,7-1H-tetrahydroindol-4-one the title compound (24 mg, 35%) was isolated as a colourless solid. mp 143–145° C. $^1$H NMR (360 MHz, $CDCl_3$) δ 1.08 (6H,s), 1.39 (9H,s), 2.40 (2H,s), 2.89 (2H,s), 6.87 (1H,s), 7.25–7.32 (2H,m), 7.83 (1H,d of t, J=7.8 and 2.0 $H_2$), 8.54–8.60 (1H,m). MS (ES$^+$) 297 (M+1).

EXAMPLE 3

3-Cyclopropyl-6,6-dimethyl-1-(pyridin-2-yl)-4,5,6 7-tetrahydroindol-4-one

Step 1: Methyl 3-cyclopropyl-6,6-dimethyl-4-oxo-4,5,6,7-tetrahydro-1H-indole-2-carboxylate Methyl 4-cyclopropyl-3-oxobutanoate (15 g, 0.106 mol) in AcOH (40 mL) was cooled to 10° C. and a solution of $NaNO_2$ (9.9 g, 0.14 mol) in water (40 mL) was added dropwise, maintaining the temperature below 20° C. After addition the mixture was warmed to 20° C., stirred for 90 min then washed with DCM (3×100 mL). The aqueous phase was separated, evaporated and the residue triturated with ether. The resultant solid was filtered off and the filtrate evaporated to afford a yellow oil. The oil was dissolved in ether, washed with water (100 mL) then the organic layer dried ($MgSO_4$) and evaporated. The oxime (18 g, 100%) was isolated as a yellow oil and used without further purification. $^1$H NMR (360 MHz, $d_6$-DMSO) δ 0.97–1.08 (4H,m), 2.69–2.79 (1H,m), 3.76 (3H,s). 12.80–13.40 (1H,br s). Sodium acetate trihydrate (17 g, 0.13 mol) and 5,5-dimethyl-1,3-cyclohexandione (14 g, 0.1 mol) in AcOH (117 mL) was heated to 70° C. A solution of the oxime (18 g, 0.1 mol) in AcOH (58 mL) was added via a dropping funnel, whilst simultaneously adding zinc dust (10 g) over a period of 15 min, maintaining the temperature between 70–80° C. The solution was heated at 100° C. for 2 h, after which time the mixture was cooled to room temperature, poured into ice-water (400 mL) and extracted with DCM (3×100 mL). The combined organic layers were washed with water (200 mL), dried ($MgSO_4$) and evaporated. The resultant yellow oil solidified on standing at 0° C., whereupon isohexane/ether was added and the resultant pyrrole (6.5 g, 25%) isolated as a colourless solid. $^1$H NMR (360 MHz, $CDCl_3$) δ 0.89–0.93 (2H,m), 1.09 (6H,s), 1.21–1.26 (2H,m), 2.33 (2H,s) 2.53–2.65 (3H,m) 3.87 (3H,s), 8.90–9.06 (1H,br s). MS (ES$^+$) 262 (M+1).

Step 2: 3-Cyclopropyl-6,6-dimethyl-4-oxo-4,5,6,7-tetrahydro-1H-indole-2-carboxylic acid In the same way as described for Intermediate 1, Step 2, using methyl 3-cyclopropyl-6,6-dimethyl-4-oxo-4,5,6,7-tetrahydro-1H-indole-2-carboxylate the acid (3.8 g, 100%) was isolated as a colourless solid. $^1$H NMR (250 MHz, $d_6$-DMSO) δ 0.70–0.79 (2H,m), 1.00 (6H,s), 1.18–1.28 (2H,m), 2.22 (2H,s), 2.63 (2H,s), 2.74–2.86 (1H,m), 11.74–11.82 (1H,br s). MS (ES$^+$) 248 (M+1).

Step 3: 3-Cyclopropyl-6,6-dimethyl-4,5,6,7-tetrahydro-1H-indol-4-one

A solution of the acid (511 mg, 2.1 mmol) in DMSO (8 mL) and water (2 mL) was heated at 150° C. for 18 h. After this time the mixture was diluted with EtOAc (50 mL) and washed with water (2×50 mL). The organic layer was separated, dried ($Na_2SO_4$) and evaporated. The residue was triturated with ether/hexane to afford the title pyrrole (197 mg, 47%) as a colourless solid. $^1$H NMR (250 MHz, $CDCl_3$) δ 0.45–0.52 (2H,m), 0.84–0.91 (2H,m), 1.10 (6H,s), 2.26–2.35 (3H,m), 2.61 (2H,s), 6.23 (1H,d, J=3 Hz), 7.94–8.22 (1H,br s). MS(ES$^+$) 204 (M+1).

Step 4: 3-Cyclopropyl-6,6-dimethyl-1-(pyridin-2-yl)-4,5,6,7-tetrahydroindol-4-one In the same way as described for example 1 using 3-cyclopropyl-6,6-dimethyl-4,5,6,7-tetrahydro-1H-indol-4-one the title compound (38 mg, 41%) was isolated as a colourless solid. $^1$H NMR (360 MHz, $CDCl_3$) δ 0.53–0.57 (2H,m), 0.90–0.94 (2H,m), 1.10 (6H,s), 2.38–2.43 (3H,m), 2.91 (2H,s), 6.68 (1H,s), 7.22–7.27 (2H,m), 7.81 (1H,d of t, J=8.1 and 2.0Hz), 8.50–8.55 (1H,m). MS (ES$^+$) 281 (M+1).

EXAMPLE 4

3-Ethyl-6,6-dimethyl-1-(pyrimidin-2-yl)-4,5,6,7-tetrahydroindol-4-one

A solution of 6,6-dimethyl-3-ethyl-4,5,6,7-tetrahydro-1H-indole-4-one (100 mg, 0.52 mmol), $K_2CO_3$ (87 mg, 0.63 mmol), copper (I) bromide (15 mg, 0.1 mmol) and 2-chloropyrimidine (71 mg, 0.63 mmol) in DMF (1 mL) were heated at 180° C. for 24 h. More copper (I) bromide (16 mg, 0.1 mmol) and 2-chloropyrimidine (50 mg) were added and heating continued for a further 24 h. The DMF was evaporated and the residue partitioned between water and DCM. The organic layer was separated and the aqueous phase extracted with DCM (2×). The combined organic layers were washed with water, dried ($MgSO_4$) and evaporated. The residue was chromatographed on silica gel, eluting with 4:1 isohexane: EtOAc, to afford the title compound (35 mg, 25%) as a yellow solid. mp 111–114° C. Found: C, 71.07; H, 6.98; N, 15.20%. Calc $C_{16}H_{19}N_3O$: C, 71.35; H, 7.11; N, 15.60%. $^1$H NMR (360 MHz, $d_6$-DMSO) δ 1.06 (6H,s), 1.15 (3H,t, J=7.4 Hz), 2.30 (2H,s), 2.67 (2H,q, J=7.3 Hz), 3.23 (2H,s), 7.44 (1H,t, J=4.8Hz), 7.47 (1H,s), 8.86 (2H,d, J=4.8Hz). MS (ES$^+$) 270 (+1).

EXAMPLE 5

6,6-Dimethyl-3-ethyl-1-(thiazol-2-yl)-4,5,6,7-tetrahydroindol-4-one

In the same way as described for Example 4 using 2-bromothiazole, the title compound (45 mg, 31%) was isolated as a cream solid. mp 58–60° C. Found: C, 64.94; H, 6.25; N, 10.27%. Calc. $C_{15}H_{18}N_2OS.0.1(H_2O)$: C, 65.23, H, 6.64; N, 10.14%. $^1$H NMR (360 MHz, $D_6$-DMSO) δ 1.06 (6H,s), 1.15 (3H,t, J=7.4 Hz), 2.31 (2H,s), 2.66 (2H,q, J=7.4 Hz), 3.01 (2H,s), 7.14 (1H,s) 7.64 (1H,d, J=3.5 Hz), 7.71 (1H,d, J=3.5 Hz). MS (ES$^+$) 275 (M+1).

EXAMPLE 6

6,6-Dimethyl-3-ethyl-1-(3-fluorophenyl)-4,5,6,7-tetrahydroindol-4-one 6,6-Dimethyl-3-ethyl-4,5,6,7-tetrahydro-1H-indol-4-one (50 mg, 0.26 mmol), copper acetate (71 mg, 0.39 mmol), 3-fluorophenyl boronic acid (73 mg, 0.52 mmol) and triethylamine (73 μL, 0.52 mmol) and triethylamine (73 μL, 0.52 mmol) in DCM (1 mL) was stirred at room temperature for 48 h. The crude reaction mixture was poured onto a bond elut tube (Anachem 1225–6034 10 g/60 mL) and eluted using isohexane : EtOAc (100:0→5:1) to afford a yellow solid. The solid was triturated in ether to afford the title compound (15 mg, 20%) as a colourless solid. $^1$H NMR (360 MHz, CDCl$_3$) δ 1.08 (6H,s), 1.22 (3H,t, J=7.4Hz), 2.36 (2H,s), 2.62 (2H,s), 2.81 (2H,q, J=7.4 Hz), 6.57 (1H,s), 7.02–7.11 (3H,m), 7.41–7.45 (1H,m). MS (ES$^+$) 286 (M+1).

EXAMPLE 7

6,6-Dimethyl-3-ethyl-1-(4-trifluoromethylphenyl)-4,5,67-tetrahydroindol-4-one

In the same way as described in Example 6 using 4-trifluoromethylbenzene boronic acid, the title compound (13 mg, 10%) was isolated as a colourless solid. $^1$H NMR (360 MHz, CDCl$_3$) δ 1.08 (6M,s), 1.23 (3H,t, J=7.4 Hz), 2.38 (2H,s), 2.64 (2H,s), 2.82 (2H,q, J=7.4 Hz), 6.60 (1H,s), 7.41 (2H,d, J=8.4 Hz), 7.75 (2H,d, J=8.4 Hz). MS (ES$^+$) 336 (M+1).

EXAMPLE 8

6,6-Dimethyl-3-ethyl-1-(4-methylphenyl)-4,5,6,7-tetrahydroindol-4-one

In the same way as described in Example 6 using 4-methylbenzene boronic acid, the title compound (65 mg, 59%) was isolated as a colourless solid. Found: C, 80.53; H, 8.30; N, 4.76%. Calc. $C_{19}H_{23}NO.0.15(H_2O)$: C, 80.33; H, 8.27; N, 4.93%. $^1$H NMR (360 MHz, CDCl$_3$) δ 1.06 (6H,s), 1.22 (2H,t, J=7.4 Hz), 2.27 (2H,s), 2.35 (3,H,s), 2.58 (2H,s), 2.80 (2H,q, J=7.4Hz), 6.53 (1H,s), 7.17 (2H,d, J=8.3 Hz), 7.26 (2H,d, J=8.3 Hz). MS (ES$^+$) 282 (M+1).

EXAMPLE 9

1-(4-Chlorophenyl)-6,6-dimethyl-3-ethyl-4,5,6,7-tetrahydroindol-4-one

In the same way as described in Example 6 using 4-chlorobenzene boronic acid, the title compound (38 mg, 32%) was isolated as a colourless solid. Found: C, 70.18; H, 6.58; N, 4.43%. Calc. $C_{18}H_{20}ClNO.0.4(H_2O)$: C, 69.96; H, 6.78; N, 4.53%. $^1$H NMR (360 MHz, CDCl$_3$) δ 1.07 (6H,s), 1.22 (3H,t, J=7.4 Hz), 2.30 (2H,s), 2.58 (2H,s), 2.80 (2H,q, J=7.4 Hz), 6.54 (1H,s), 7.24 (1H,d, J=8.7 Hz), 7.44 (IH,d, J=8.7Hz). MS (ES$^+$) 302/304 (M+1).

EXAMPLE 10

6,6-Dimethyl-3-ethyl-1-(4-fluorophenyl)-4,5,6,7-tetrahydroindol-4-one

In the same way as described in Example 6 using 4-fluorobenzene boronic acid, the title compound (50 mg, 45%) was isolated as a colourless solid. Found: C, 74.76; H, 6.98; N, 4.80%. Calc. $C_{18}H_{20}FNO.0.2(H_2O)$: C, 74.82; H, 7.12; N, 4.85%. $^1$H NMR (360 MHz, $d_6$-DMSO) δ 0.99 (6H,s), 1.15 (3H,t, J=7.5 Hz), 2.25 (2H,s), 2.63 (2H,s), 2.66 (2H,q, J=7.5 Hz), 6.79 (1H,s), 7.37 (2H,dd, J=8.7 and 8.7Hz), 7.49 (2H,dd, J=8.7 and 4.9 Hz). MS (ES$^+$) 286 (M+1).

EXAMPLE 11

6,6-Dimethyl-3-ethyl-1-(3-methylphenyl)-4,5,6,7-tetrahydroindol-4-one

In the same way as described in Example 6 using 3-methylbenzene boronic acid, the title compound (50 mg, 31%) was isolated as a colourless solid. $^1$H NMR (360 MHz, CDCl$_3$) δ1.07 (6H,s), 1.23 (3H,t, J=7.5 Hz), 2.31 (2H,s), 2.43 (3H,s), 2.59 (2H,s), 2.81 (2H,q, J=7.5 Hz), 6.55 (1H,s), 7.07–7.11 (2H,m), 7.19 (1H,d, J=7.5 Hz). 7.35 (1H,dd, J=7.6 and 7.6 Hz). MS (ES$^+$) 282 (M+1).

EXAMPLE 12

6,6-Dimethyl-3-methylthio-1-(pyridin-2-yl)-4,5,6,7-tetrahydroindol-4-one

Step 1: 6,6-Dimethyl-4,5,6,7-tetrahydro-1H-indol-4-one

A solution of 5,5-dimethyl-1,3-cyclohexandione (30 g, 0.21 mol), aminoacetaldehyde dimethyl acetal (35 mL, 0.32 mol) and p-toluenesulphonic acid hydrate (1.5 g, 8 mmol) in toluene (250 mL) were heated at reflux for 4 h using Dean-Stark apparatus to remove the water. The toluene was evaporated and the residue dissolved in 3N HCl (250 mL). The solution was heated at 60° C. for 6 h. After this time the mixture was cooled to room temperature and extracted with DCM (6×). The combined organic layers were dried (MgSO$_4$), evaporated and the residue chromatographed on silica gel, eluting with isohexane: EtOAc (4:1→1:1). The fractions containing the desired product were combined, evaporated and the residue triturated with ether. The title compound (1.8 g, 5%) was isolated as a cream solid. mp 177–178° C. $^1$H NMR (360 MHz, $d_6$-DMSO) 8 1.02 (6H,s), 2.19 (2H,s), 2.63 (2H,s), 6.23 (1H,t, J=3.9 Hz), 6.71 (1H,t, J=3.9 Hz). MS (ES$^+$) 164 (M+1).

Step 2: 6,6-Dimethyl-2-thiocyanato-4,5,6,7-tetrahydro-1H-indol-4-one

Potassium thiocyanate (1.2 g, 12.3 mmol) was dissolved in MeOH (4 mL) and cooled to −70° C. The mixture was treated with bromine (0.31 mL, 6.1 mmol), maintaining the temperature below −60° C. After addition the mixture was warmed to −30° C. and a solution of the indolone (1 g, 6.1 mmol) in MeOH (25 mL) was added dropwise. The mixture was stirred for 30 min at −30° C. then allowed to warm to room temperature and stirred for 3 h. The mixture was poured onto ice water (30 mL), the MeOH evaporated and the aqueous phase extracted with DCM (2×). The combined organic layers were washed with water, NaHCO$_3$ (sat.) then separated and dried (Na$_2$SO$_4$). The solvent was evaporated and the residue triturated with ether. The title compound (0.83 g, 62%) was isolated as a beige solid. $^1$H NMR (360 MHz, $d_6$-DMSO) δ 1.03 (6H,s) 2.25 (2H,s), 2.68 (2H,s), 6.83 (1H,d, J=1.9 Hz), 12.44 (1H,br s). MS (ES$^+$) 221 (M+1).

Step 3: 6,6-Dimethyl-2-methylthio-4,5,6,7-tetrahydro-1H-indol-4-one

To a stirred solution of 6,6-dimethyl-2-thiocyanato-4,5,6, 7-tetrahydro-1H-indol-4-one (400 mg, 1.8 mmol) and MeI (124 μL, 2.0 mmol) in MeOH (10 mL) at −5° C. was added a solution of KOH (117 mg, 2.1 mmol) in 1:1 MeOH/water (6 mL), maintaining the temperature below 0° C. The mixture was stirred for 3 h at room temperature, after which time the MeOH was removed and the residue partitioned between DCM and water. The organic layer was separated and the aqueous phase re-extracted with DCM. The combined organic layers were dried ($Na_2SO_4$) and evaporated to afford the title compound (350 mg, 88%) as a colourless solid. mp 195–196° C. Found: C, 62.20; H, 7.13; N, 6.34%. Calc. $C_{11}H_{15}NOS.0.2(H_2O)$: C, 62.06; H, 7.29; N, 6.58%. $^1$H NMR (360 MHz, $d_6$-DMSO) δ 1.02 (6H,s), 2.19 (2H,s), 2.34 (3H,s), 2.61 (2H,s), 6.30 (1H,d, J=2.4 Hz), 11.59 (1H,br s). MS ($ES^+$) 210 (M+1).

Step 4: 6,6-Dimethyl-3-methylthio-4,5,6,7-tetrahydro-1H-indol-4-one 6,6-Dimethyl-2-methylthio-4,5,6,7-tetrahydro-1H-indol-4-one (350 mg, 1.7 mmol) was heated at reflux in trifluoroacetic acid (4 mL) and 1,2-dichloroethane (4 mL) for 5 h. After this time the mixture was evaporated and the residue partitioned between water (10 mL) and DCM (10 mL). The organic layer was separated and the aqueous phase extracted with DCM (2×). The combined organic layers were dried ($Na_2SO_4$) and evaporated. The residue was chromatographed on silica gel, eluting with hexane: EtOAc (4:1), to afford the title compound (60 mg, 17%) as a pink solid. $^1$H NMR (360 MHz, $d_6$-DMSO) δ 1.01 (6H,s), 2.18 (2H,s), 2.27 (3H,s), 2.61 (2H,s), 6.53 (1H,d, J=2.2 Hz), 11.31 (1H,br s). MS ($ES^+$) 210 (M+1).

Step 5: 6,6-Dimethyl-3-methylthio-1-(pyridin-2-yl)-4,5,6,7-tetrahydroindol-4-one In the same way as described in Example 1 using 6,6-dimethyl-3-methylthio-4,5,6,7-tetrahydro-1H-indol-4-one, the title compound (20 mg, 30%) was isolated as a colourless solid. $^1$HNMR (360 MHz, $d_6$-DMSO) δ 0.97 (6H,s) 2.24 (2H,s) 2.30 (3H,s), 2.92 (2H,s), 7.03 (1H,s), 7.37 (1H,dd, J=7.1 and 5.0 Hz), 7.60 (1H,d, J=8.1 Hz), 7.95 (1H,d of t, J=7.7 and 1.9 Hz), 8.50–8.53 (1H,m). MS ($ES^+$) 287 (M+1).

EXAMPLE 13

6.6-Dimethyl-3-ethylthio-1-(pyridin-2-yl)-4,5,6,7-tetrahydroindol-4-one

Step 1: 6,6-Dimethyl-2-ethylthio-4,5,6,7-tetrahydro-1H-indol-4-one

In the same way as described for Example 12, Step 3 using ethyl iodide, the title compound (385 mg, 48%) was isolated as a colourless solid. $^1$H NMR (360 MHz, $d_6$-DMSO) δ 1.02 (6H,s), 1.13 (3H,t, J=7.2 Hz), 2.20 (2H,s), 2.62 (2H,s), 2.68 (2H,q, J=7.2 Hz), 6.36 (1H,d, J=2.3 Hz), 11.56 (1H,br s). MS ($ES^+$) 224 (M+1).

Step 2: 6,6-Dimethyl-3-ethylthio-4,5,6,7-tetrahydro-1H-indol-4-one

In the same way as described in Example 12, Step 4 using 6,6-dimethyl-2-ethylthio-4,5,6,7-tetrahydro-1H-indol-4-one, the title compound (100 mg, 26%) was isolated as a colourless solid. $^1$H NMR (360 MHz, $d_6$-DMSO) δ 1.01 (6H,s), 1.14 (3H,t, J=7.4 Hz), 2.19 (2H,s), 2.62 (2H,s), 2.75 (2H,q, J=7.2 Hz), 6.64 (1H,d, J=2.3 Hz), 11.33 (1H,br s). MS ($ES^+$) 224 (M+1).

Step 3: 6,6-Dimethyl-3-ethylthio-l-(pyridin-2-yl)-4,5,6,7-tetrahydroindol-4-one

In the same way as described in Example 1 using 6,6-dimethyl-3-ethylthio-4,5,6,7-tetrahydro-1H-indol-4-one, the title compound (80 mg, 60%) was isolated as a cream solid. mp 158–159° C. Found: C, 67.49; H, 6.60; N, 9.08%. Calc. $C_{17}H_{20}N_2OS.0.1(H_2O)$: C, 67.56; H, 6.74; N, 9.27%. $^1$H NMR (360 MHz, $d_6$-DMSO) δ 1.02 (6H,s), 1.25 (3H,t, J=7.3 Hz), 2.30 (2H,s), 2.86 (2H,q, J=7.3 Hz), 2.97 (2H,s), 7.18 (1H,s), 7.43 (1H,dd, J=7.5 and 4.9 Hz), 7.65 (1H,d, J=8.1 Hz), 8.02 (1H,d of t, J=7.9 and 1.9 Hz), 8.57–8.62 (1H,m). MS ($ES^+$) 301 (M+1).

EXAMPLE 14

6,6-Dimethyl-3(phenylmethyl)thio-1-(pyridin-2-yl)-4,5,6,7-tetrahydroindol-4-one

Step 1: 6,6-Dimethyl-2-(phenylmethyl)thio-4,5,6,7-tetrahydro-1H-indol-4-one

In the same way as described for Example 12, Step 3 using benzyl bromide, the title compound (457 mg, 72%) was obtained as a cream solid. mp 148–150° C. Found: C, 70.90; H, 6.46; N, 5.02%. Calc. $C_{17}H_{19}NOS.0.15(H_2O)$: C, 70.87; H, 6.75; N, 4.86%. H NMR (360 MHz, $CDCl_3$) 1.07 (6H,s), 2.31 (2H,s), 2.47 (2H,s), 3.82 (2H,s), 6.67 ((H,d, J=2.4 Hz), 7.08–7.12 (2H,m), 7.23–7.26 (3H,m), 7.56 (1H, br s). MS ($ES^+$) 286 (M+1).

Step 2: 6,6-Dimethyl-3-(phenylmethyl)thio-4,5,6,7-tetrahydro-1H-indol-4-one

In the same way as described in Example 12, Step 4 using 6,6-dimethyl-2(phenylmethyl)thio-4,5,6,7-tetrahydro-1H-indol-4-one, the title compound (64 mg, 15%) was isolated as a cream solid. mp 220–223° C. Found: C, 68.43; H, 6.31; N, 4.66%. Calc. $C_{17}H_{19}NOS.0.65(H_2O)$: C, 68.72; H, 6.89; N, 4.71%. $^1$H NMR (360 MHz, $CDCl_3+d_4$-MeOH) δ 1.00 (6H,s), 2.24 (2H,s), 2.53 (2H,s), 3.92 (2H,s), 6.34 (1H,s), 7.04–7.11 (5H,m). MS ($ES^+$) 286 (M+1).

Step 3: 6,6-Dimethyl-3(phenylmethyl)thio-1-(pyridin-2-yl)-4,5,6,7-tetrahydroindol-4-one In the same way as described in Example 1 using 6,6-dimethyl-3-(phenylmethyl)thio-4,5,6,7-tetrahydro-1H-indol-4-one, the title compound (17 mg, 27%) was obtained as a cream solid. mp 190–192° C. Found: C, 70.66; H, 5.84; N, 7.50%. Calc. $C_{22}H_{22}N_2OS.0.1(CH_2Cl_2).0.2(H_2O)$: C, 70.86; H, 6.08; N, 7.48%. $^1$H NMR (360 MHz, $CDCl_3$) δ 1.11 (6H,s), 2.43 (2H,s), 2.94 (2H,s), 4.14 (2H,s), 6.89 (1H,s), 7.19–7.34 (7H,m), 7.79–7.84 (1H,m), 8.52–8.56 (1H,m). MS ($ES^+$) 363 (M+1).

EXAMPLE 15

6,6-Dimethyl-1-(pyridin-2-yl)-3-(thiazol-2-yl)-4,5,6,7-tetrahydroindol-4-one

Step 1: 6,6-Dimethyl-1-(triisopropylsilyl)-4,5,6,7-tetrahydroindol-4-one

A solution of 6,6-dimethyl-4,5,6,7-tetrahydro-1H-indol-4-one (3.8 g, 23 mmol) in DMF (25 mL) was cooled to 0° C. and NaH (1.02 g of a 60% dispersion in mineral oil, 26 mmol) was added portionwise. The mixture was stirred for 30 min then triisopropylsilyl chloride (5.6 mL, 26 mmol) was added at 0° C. and stirring continued for 1 hr. The mixture was warmed to room temperature then extracted with ether (3×). The combined organic layers were dried ($MgSO_4$) and evaporated. The residue was chromatographed on silica gel, eluting with isohexane: EtOAc (9:1), to give the title compound (2.9 g, 39%) as a colourless solid. $^1$H NMR (360 MHz, $CDCl_3$) δ 1.11 (6H,s), 1.14 (18H,d, J 7.5 Hz) 1.51 (3H,heptet, J=7.5 Hz), 2.34 (2H,s), 2.71 (2H,s), 6.64 (1H,d, J=3.1 Hz), 6.71 (1H,d, J=3.1 Hz). MS ($ES^+$) 320 (M+1).

Step 2: 3-Bromo-6,6-dimethyl-4,5,6,7-tetrahydro-1H-indol-4-one

A solution of 6,6-dimethyl-1-(triisopropylsilyl)-4,5,6,7-tetrahydroindol-4-one (410 mg, 1.28 mmol) in THF (20 mL) was cooled to −70° C. and N-bromosuccinimide (228 mg, 1.28 mmol) was added. Stirring was continued at −70° C. for 1 h then warmed to room temperature. After attaining room temperature, tetrabutylammonium fluoride (1.28 mL of a 1.0

M solution in THF, 1.28 mmol) was added and stirring continued for 5 min. Ether (20 mL) was added, followed by water, and the organic layer separated. The aqueous phase was extracted with ether and the combined organic layers were dried (MgSO$_4$) and evaporated. The residue was purified on silica gel, eluting with DCM, to give the title compound (210 mg, 68%) as a colourless solid. $^1$H NMR (360 MHz, d$_6$-DMSO) δ 1.02 (6H,s), 2.22 (2H,s), 2.64 (2H,s), 6.89 (1H,d, J=2.4 Hz), 11.58 (1H,br s). MS (ES$^+$) 242/244 (M+1).

Step 3: 3-Bromo-6,6-dimethyl-1-(pyridin-2-yl)-4,5,6,7-tetrahydroindol-4-one

In the same way as described in Example 1 using 3-bromo-6,6-dimethyl-4,5,6,7-tetrahydro-1H-indol-4-one, the title compound (600 mg, 61%) was isolated as a pale yellow solid. mp 168–170° C. Found: C, 56.00; H, 4.64; N, 8.75%. Calc. C$_{15}$H$_{15}$BrN$_2$O. 0.1 (H$_2$O): C, 56.13; H, 4.77; N, 8.73%. $^1$HNMR (360 MHz, d$_6$-DMSO) δ 1.03 (6H,s), 2.33 (2H,s), 2.98 (2H,s), 7.47 (1H,dd, J=7.5 and 5.5 Hz). 7.55 (1H,s). 7.66 (1H,d, J=8.3 Hz), 8.04 (1H,d or t, J 7.7 and 1.9 Hz), 8.57-8.62 (1H,m), MS (ES$^+$) 319/321 (M+1).

Step 4: 6 6-Dimethyl-1-(pyridin-2-yl)-3-(thiazol-2-yl)-4,5,6,7-tetrahydroindol-4-one A solution of 3-bromo-6,6-dimethyl-1-(pyridin-2-yl)-4,5,6,7-tetrahydroindol-4-one (100 mg, 0.31 mmol) and 2-(n-tributylstannyl) thiazole (175 mg, 0.47 mmol) in dioxan (10 mL) was degassed with nitrogen from 30 min. Tetrakis (triphenylphosphine) palladium (75 mg, 0.06 mmol) was added and the mixture heated at reflux for 24 h. The solvent was evaporated and the residue purified on silica gel, eluting with isohexane: EtOAc (9:1→1:1). The fractions containing the desired product were combined and evaporated. The resultant orange solid was triturated with isohexane and the title compound (75 mg, 74%) isolated as a cream solid. mp 166–168° C. Found: C, 66.26; H, 5.27; N, 12.66%. Calc. C$_{18}$H$_{17}$N$_3$OS.0.2(H$_2$O): C, 66.11; H, 5.36; N, 12.85%. $^1$H NMR (360 MHz, CDCl$_3$) δ 1.15 (6H,s), 2.50 (2H,s), 3.04 (2H,s), 7.31–7.35 (2H,m), 7.45 (1H,d, J=6.3 Hz), 7.78 (1H,d, J=3.2Hz), 7.86 (1H,d of t, J=7.8 and 1.9Hz), 7.91 (1H,s), 8.56–8.60 (1H,m). MS (ES$^+$) 324 (M+1).

EXAMPLE 16

6,6-Dimethyl-3-phenyl-1-(pyridin-2-yl)-4,5,6,7-tetrahydroindol-4-one

A solution of 3-bromo-6,6-dimethyl-1-(pyridin-2-yl)-4,5,6,7-tetrahydroindol-4-one (100 mg, 0.31 mmol), phenylboronic acid (153 mg, 1.25 mmol), tetrakis (triphenylphosphine)palladium (50 mg, 0.04 mmol) and Na$_2$CO$_3$ (197 mg, 1.9 mmol) in ethylene glycol dimethyl ether (10 mL) and water (4 mL) was heated at reflux for 8 h. The solvent was evaporated and the residue partitioned between DCM and aqueous K$_2$CO$_3$ (10% ($^w$/v)). The organic layer was separated and the aqueous phase re-extracted with DCM (2x). The combined organic layers were washed with water, dried (MgSO$_4$) and evaporated. The residue was chromatographed on silica gel, eluting with isohexane: EtOAc (9:1), to afford the title compound (60 mg, 61%) as a yellow solid. mp 160–162° C. Found: C, 78.23; H, 6.26; N, 8.57%. Calc. C$_{21}$H$_{20}$N$_2$O.0.35(H$_2$O): C, 78.16; H, 6.47; N, 8.68%. $^1$H NMR (360 MHz, CDCl$_3$) δ 1.13 (6H,s), 2.45 (2H,s), 2.99 (2H,s), 7.17 (1H,s), 7.24–7.38 (5H,m), 7.67 (2H,d, J=7.2 Hz), 7.86 (1H,d of t, J=7.9 and 1.9 Hz), 8.56–8.61 (1H,m). MS (ES$^+$) 317 (M+1).

EXAMPLE 17

6,6-Dimethyl-1-(pyridin-2-yl)-3-(pyridin-2-yl)-4,5,6,7-tetrahydroindol-4-one

In the same way as described in Example 15, Step 4 using 2-(tributylstannyl)pyridine, the title compound (40 mg, 40%) was isolated as a cream solid. mp 171–174° C. Found: C, 74.55; H, 5.89; N, 12.61%. Calc. C$_{20}$H$_{19}$N$_3$O.0.35(H$_2$O): C, 74.21; H, 6.13; N, 12.98%. $^1$HNMR (360 MHz, CDCl$_3$) δ 6 1.14 (6H,s), 2.49 (2H,s), 3.03 (2H,s), 7.15 (1H,dd, J=6.3 and 3.8 Hz), 7.31 (1H,dd, J=7.5 and 4.9 Hz), 7.48 (1H,d, J=8.2 Hz), 7.70–7.73 (2H,m), 7.86 (1H,d of t, J=7.8 and 1.9Hz), 8.32 (1H,d, J=8.1 Hz), 8.55–8.59 (2H,m). MS (ES$^+$). 318 (M+1).

EXAMPLE 18

6,6-Dimethyl-1-(pyridin-2-yl)-3-vinyl-4,5,6,7-tetrahydroindol-4-one

In the same way as described in Example 15, Step 4 using tributyl(vinyl)tin, the title compound (45 mg, 54%) was isolated as a cream solid. mp 150–154° C. $^1$H NMR (360 MHz, CDCl$_3$) δ 1.11 (6H,s), 2.40 (2H,s), 2.93 (2H,s), 5.18 (1H,dd, J=11 and 1.8 Hz), 5.72 (1H,dd, J=18 and 1.8 Hz), 7.22 (1H,dd, J=18 and 11 Hz), 7.26-7.35 (3H,m), 7.85 (1H,d of t, J=7.7 and 1.9 Hz), 8.55–8.58 (1H,m). MS (ES$^+$) 267 (M+1).

EXAMPLE 19

6,6-Dimethyl-3-phenylmethyl-1-(pyridin-2-yl)-4,5,6,7-tetrahydroindol-4-one

A solution of 3-bromo-6,6-dimethyl-1-(pyridin-2-yl)-4,5,6,7-tetrahydroindol-4-one (10 mg, 0.31 mmol), benzyltributylstannane (253 mg, 0.68 mmol) and dichlorobis (triphenylphosphine)palladium (50 mg, 0.08 mmol) in hexamethylphosphoramide (1 mL) was heated at 70° C. for 48 h. The mixture was cooled to room temperature, diluted with DCM (2 mL), and the solution chromatographed on silica gel, eluting with isohexane: EtOAc (4:1). The title compound (45 mg, 43%) was isolated as a colourless solid. mp 111–113° C. Found: C, 79.7; H, 6.7; N, 8.3%. Calc. C$_{22}$H$_{22}$N$_2$O: C, 79.97; H, 6.71; N, 8.48%. $^1$H NMR (360 MHz, CDCl$_3$) δ 1.11 (6H,s), 2.39 (2H,s), 2.93 (2H,s), 4.17 (2H,s), 6.61 (1H,s), 7.16–7.34 (7H,m), 7.77 (1H, d of t, J=7.7 and 1.9 Hz), 8.50–8.53 (1H,m). MS (ES$^+$) 331 (M+1).

EXAMPLE 20

6,6-Dimethyl-3-(oxazol-2-yl)-1-(pyrdin-2-yl)-4 5, 6 7-tetrahydroindol-4-one

In the same way as described in Example 15, Step 4 using 2-tributylstannyloxazole, the title compound (50 mg, 52%) was afforded as a cream solid. mp 194–196° C. Found: C, 70.30; H, 5.25; N, 13.48%. Calc. C$_{18}$H$_{17}$N$_3$O$_2$: C, 70.34; H, 5.58; N, 13.67%. $^1$H NMR (400 MHz, CDCl$_3$) δ 1.13 (6H,s), 2.50 (2H,s), 3.00 (2H,s), 7.20 (1H,s), 7.36 (1H,dd, J=6.7 and 4.3 Hz), 7.41 (1H,d, J=7.4 Hz), 7.73 (1H,s), 7.75 (1H,s), 7.89 (1H,d of t, J=6.9 and 1.7Hz), 8.57–8.60 (1H,m). MS (ES$^+$) 308 (M+1).

EXAMPLE 21

6,6-Dimethyl-1-(pyridin-2-yl)-3-(thiazol-5-yl)-4,5,6,7-tetrahydroindol-4-one

In the same way as described in Example 15, Step 4 using 5-tributylstannylthiazole, the title compound (73 mg, 72%) was obtained as a yellow solid. mp 167–169° C. Found: C, 64.96; H, 5.23; N, 12.01%. Calc. C$_{18}$H$_{17}$N$_3$OS.0.1(Et$_2$O) .0.45 (H$_2$O): C, 65.20; H, 5.62; N, 12.40%. $^1$H NMR (400 MHz, CDCl$_3$) δ 1.14 (6H,s), 2.47 (2H,s), 2.97 (2H,s), 7.33–7.39 (3H,m), 7.90 (1H,d of t, J=7.7 and 1.9 Hz), 8.41 (1H,s), 8.57–8.60 (1H,m), 8.70 (1H,s). MS (ES$^+$) 324 (M+1).

EXAMPLE 22

6,6-Dimethyl-3-phenylamino-1-(pyridin-2-yl)-4,5,6,7-tetrahydroindol-4-one

A suspension of 3-bromo-6,6-dimethyl-1-(pyridin-2-yl)-4,5,6,7-tetrahydroindol-4-one (50 mg, 0.16mmol), aniline (17 µL, 0.19 mmol), sodium tert-butoxide (18 mg, 0.19 mmol) tris(dibenzylideneacetone)dipalladium (7.2 mg, 0.008mmol) and (R)-(+)-2,2'-bis(diphenylphosphino)-1,1-binaphthyl (9.8 mg, 0.016 mmol) in toluene (3 mL) was heated at reflux for 3 h. The toluene was evaporated and the residue chromatographed on silica gel, eluting with isohexane: EtOAc (9:1→4:1). The title compound (23 mg, 43%) was isolated as a yellow solid. mp 135–138° C. Found: C, 73.98; H, 6.10; N, 12.33%. $C_{21}H_{21}N_3O0.0.45(H_2O)$: C,74.29; H, 6.50; N, 12.38%. $^1$H NMR (360 MHz, $d_6$-DMSO) δ 1.07 (6H,s), 2.37 (2H,s), 3.03 (2H,s), 6.81 (1H,t, J=7.4 Hz), 7.08 (2H,d, J=7.7 Hz), 7.25–7.29 (2H,m), 7.41 (1H,dd, J=7.2 and and 4.9Hz), 7.72 (1H,d, J=8.1 Hz), 8.01 (1H,d of t, J=7.6 and 1.8 Hz), 8.16 (1H,s), 8.57–8.60 (1H,m). MS (ES$^+$) 332 (M+1).

EXAMPLE 23

6,6-Dimethyl-1-(pyridin-2-yl)-3-(pyridin-2-ylamino)-4,5,6,7-tetrahydroindol-4-one In the same way as described in Example 22 using 2-aminopyridine, the title compound (20 mg, 23%) was isolated as a yellow solid. mp 180–183° C. $^1$H NMR (360 MHz, CDCl$_3$) δ 1.13 (6H,s), 2.41 (2H,s), 3.04 (2H,s), 6.65–6.69 (1H,m), 6.73 (1H,d, J=8.5 Hz), 7.24 (1H,dd, J=7.4 and 4.9 Hz), 7.44–7.48 (2H,m), 7.83 (1H,d of t, J=7.9 and 1.9 Hz) 7.91 (1H,s), 8.26–8.30 (1H,m), 8.53–8.57 (1H,m), 8.74 (1H,s). MS (ES$^+$) 333 (M+1).

EXAMPLE 24

6,6-Dimethyl-3-ethyl-1-(6-methylpyridin-2-yl)-4,5,6,7-tetrahydroindol-4-one

In the same way as described in Example 1 using 2-fluoro-6-methylpyridine, the title compound (15 mg, 17%) was isolated as a cream solid. $^1$H NMR (360 MHz, CDCl$_3$) δ 1.09 (6H,s), 1.23 (3H,t, J=7.4 Hz) 2.37 (2H,s), 2.58 (3H,s), 2.81 (2H,q, J=7.4Hz), 2.89 (2H,s), 6.89 (1H,s), 7.07–7.12 (2H,m), 7.69 (1H,t, J=7.8 Hz). MS (ES$^+$) 283 (M+1).

EXAMPLE 25

6,6-Dimethyl-3-(4-methylthiazol-5-yl)-1-(pyridin-2-yl)-4,5,6,7-tetrahydroindol-4-one In the same way as described in Example 15, Step 4 using 2-(tributylstannyl)-4-methylthiazole the title compound (52 mg, 19 mg) was isolated. $^1$H NMR (400 MHz, $d_6$-DMSO) δ 1.06 (6H,s), 2.37 (3H,s), 2.43 (2H,s), 3.01 (2H,s) 7.16 (1H,s), 7.50 (1H,dd, J=7.3 and 4.9 Hz), 7.77 (1H,d, J=8.2 Hz), 7.94 (1H,s), 8.06 (1H,d of t, J=8.0 and 1.7 Hz), 8.61–8.63 (1H,m). MS (ES$^+$) 338 (M+1).

EXAMPLE 26

3-(4-Chlorophenyl)-6,6-dimethyl-1-(pyridin-2-yl)-4,5,6,7-tetrahydroindol-4-one A solution of 3-bromo-6,6-dimethyl-1-(pyridin-2-yl)-4,5,6,7-tetrahydroindol-4-one (50 mg, 0.16 mmol) and tetrakis(triphenylphosphine)palladium (15 mg, 0.01 mmol) in ethylene glycol dimethyl ether (2 mL) at 45° C. was degassed with nitrogen for 30 min. A degassed solution of Cs$_2$CO$_3$ (104 mg, 0.16 mmol) in water (1 mL) was added followed by 4-chlorophenylboronic acid (25 mg, 0. 16 mmol). The solution was heated at 100° C. for 18 h then filtered through celite. The filtrate was partitioned between DCM and water. The organic phase was separated, dried (MgSO$_4$) and evaporated. The residue was purified by column chromatography, eluting with isohexane: EtOAc (3:1) to give the title compound (6 mg, 11%) as a colourless solid. $^1$H NMR (360 MHz, $d_6$-DMSO) δ 1.05 (6H,s), 2.37 (2H,s), 3.01 (2H,s), 7.38 (2H,d, J=8.5 Hz), 7.46–7.50 (1H,m), 7.56 (1H,s), 7.68–7.74 (3H,m), 8.05–8.09 (1H,m), 8.59–8.63 (1H,m). MS (ES$^+$) 351/353 (M+1).

EXAMPLE 27

3-(3-Chlorophenyl)-6,6-dimethyl-1-(pyridin-2-yl)-4,5,6,7-tetrahydroindol-4-one In the same way as described in Example 26 using 3-chlorophenylboronic acid, the title compound (71 mg, 43%) was isolated as a colourless solid. $^1$H NMR (360 MHz, CDCl$_3$) δ 1.13 (6H,s), 2.46 (2H,s), 2.98 (2H,s), 7.20 (1H,s), 7.23–7.39 (4H,m), 7.60 (1H,t of d, J=7.3 and 1.5 Hz), 7.66 (1H,t, J=1.8 Hz), 7.88 (1H,d of t, J=7.9 and 1.9 Hz), 8.57–8.60 (1H,m). MS (ES$^+$) 351/353 (M+1).

EXAMPLE 28

3-(2-Chlorophenyl)-6,6-dimethyl-1-(pyridin-2-yl)-4,5,6,7-tetrahydroindol-4-one In the same way as described in Example 26 using 2-chlorophenylboronic acid, the title compound (44 mg, 27%) was isolated as a colourless solid. $^1$H NMR (400 MHz, CDCl$_3$) δ 1.14 (6H,s), 2.40 (2H,s), 3.02 (2H,s), 7.16 (1H,s), 7.23–7.26 (2H,m), 7.30 (1H,dd, J=7.4 and 5.0 Hz), 7.38 (1H,d, J=8.1 Hz), 7.41–7.44 (2H,m), 7.87 (1H,d of t, J=7.6 and 1.9 Hz), 8.56–8.58 (1H,m). MS (ES$^+$) 351/353 (M+1).

EXAMPLE 29

6,6-Dimethyl-1-(pyridin-3-yl)-3-(thiazol-2-yl)-4,5,6,7-tetrahydroindol-4-one Step 1: 3-Bromo-6,6-dimethyl-1-(pyridin-3-yl)-4 5 6,7-tetrahydroindol-4-one In the same way as described in Example 4 using 3-bromopyridine, the title compound (72 mg, 8%) was isolated as a brown solid. $^1$H NMR (360 MHz, $d_6$-DMSO) δ 1.00 (6H,s) 2.31 (2H,s), 2.71 (2H,s), 7.40 (1H,s), 7.60 (1H,dd, J=8.4 and 4.8 Hz), 7.95–7.99 (1H,m), 8.67–8.70 (1H,m), 8.73–8.76 (1H,m). MS (ES$^+$) 319/321 (M+1)

Step 2: 6,6-Dimethyl-1-(pyridin-3-yl)-3-(thiazol-2-yl)-4,5,6,7-tetrahydroindol-4-one In the same way as described in Example 15, Step 4 using 6,6-dimethyl-1-pyridin-3-yl)-3-(thiazol-2-yl-4,5,6,7-tetrahydroindol-4-one and 2-tributylstannylthiazole, the title compound (12 mg, 10%) was isolated as a colourless solid. $^1$H NMR (400 MHz, $d_6$-DMSO) δ 1.05 (6H,s), 2.42 (2H,s), 2.75 (2H,s) 7.61–7.65 (2H,m), 7.78–7.81 (2H,m), 8.05–8.08 (1H,m), 8.70–8.71 (1H,m). MS (ES$^+$) 324 (M+1).

EXAMPLE 30

1-(5-Chloropyridin-2-yl)-6,6-dimethyl-3-(thiazol-2-yl)-4,5,6,7-tetrahydroindol-4-one Step 1: 3-Bromo-1-(5-chloropyridin-2-yl)-6,6-dimethyl-4,5,6,7-tetrahydroindol-4-one In the same way as described in Example 1 using 3-bromo-6,6-dimethyl-1,2,3,4-tetrahydro-1H-indol-4-one and 2,5-dichloropyridine, the title compound (212 mg, 36%) was isolated as a yellow solid.

Step 2: 1-(5-Chloropyridin-2-yl)-6,6-dimethyl-3-(thiazol-2-yl)-4,5,6,7-tetrahydroindol-4-one In the same way as described in Example 15, Step 4 using 3-bromo-1-(5-chloropyridin-2-yl)-6,6-dimethyl-4,5,6,7-tetrahydroindol-4-one and 2-tributylstannylthiazole, the title compound (73 mg, 37%) was isolated as a pale yellow solid. $^1$H NMR (400 MHz, $d_6$-DMSO) δ 1.06 (6H,s), 2.44 (2H,s), 3.01 (2H,s), 7.63 (1H,d, J=3Hz), 7.80–7.84 (2H,m), 8.00 (1H,s), 8.20 (1H,dd, J=8.6 and 2.6 Hz), 8.69 (1H,d, J=2.6Hz). MS (ES$^+$) 358/360 (M+1). $^1$H NMR (400 MHz, $d_6$-DMSO) δ 1.02 (6H,s), 2.33 (2H,s), 2.97 (2H,s), 7.56 (1H,s), 7.71 (1H,d, J=8.6 Hz), 8.18 (1H,dd, J=8.7Hz and 2.6 Hz), 8.64 (1H,d, J=2.6 Hz). MS (ES$^+$) 353/355 (M+1).

EXAMPLE 31

6,6-Dimethyl-3-(thiazol-2-yl)-1-(6-(thiazol-2-yl) pyridin-2-yl)-4,5,6,7-tetrahydroindol-4-one Step 1: 3-Bromo-1-(6-chloropyridin-2-yl)-6,6-dimethyl-1,2,3,4-tetrahydroindol-4-one In the same way as described in Example 1 using 3-bromo-6,6-dimethyl-1,2,3,4-tetrahydro-1H-indol-4-one and 2,6-dichloropyridine, the title compound (232 mg, 40%) was isolated as a yellow solid. $^1$H NMR (400 MHz, CDCl$_3$) δ 1.14 (6H,s), 2.42 (2H,s), 2.96 (2H,s), 7.17 (1H,s), 7.22 (1H,d, J 8.0 Hz), 7.33 (1H,d, J 7.9 Hz), 7.82 (1H,t, J=7.8Hz). MS (ES$^+$) 353/355 (M+1).

Step 2: 6,6-Dimethyl-3-(thiazol-2-yl)-1-(6-(thiazol-2-yl) pyridin-2-yl)-4,5,6,7-tetrahydroindol-4-one In the same way as described in Example 15, Step 4 using 3-bromo-1-(6-chloropyridin-2-yl)-6,6-dimethyl-1,2,3,4-tetrahydroindol-4-one and 2-tributylstannylthiazole, the title compound (35 mg; 13%) was isolated as a yellow solid. $^1$H NMR (400 MHz, CDCl$_3$) δ 1.21 (6H,s), 2.55 (2H,s), 3.24 (2H,s) 7.35 (1H,d, J=3.1 Hz), 7.50–7.53 (2H,m), 7.81 (1H,d, J=3.1 Hz), 7.97–8.02 (3H,m), 8.20 (1H,d, J=7.8 Hz). MS (ES$^+$) 407 (M+1).

EXAMPLE 32

1-(2-Cyanophenyl)-6,6-dimethyl-3-(thiazol-2-yl)-4,5,6,7-tetrahydroindol-4-one

Step 1: 3-Bromo-1-(2-cyanophenyl)-6,6-dimethyl-4,5,6,7-tetrahydroindol-4-one

A solution of 3-bromo-6,6-dimethyl-4,5,6,7-tetrahydro-1H-indol-4-one (670 mg, 2.77 mmol), 2-fluorobenzonitrile (0.3 mL, 2.77mmol) and K$_2$CO$_3$ (957 mg, 6.9 mmol) in DMSO (10 mL) was stirred at 100° C. for 3 h. The mixture was cooled to room temperature, poured into water and extracted into EtOAc (3×). The combined organic layers were washed with water (2×), dried (MgSO$_4$) and evaporated. The title compound (858 mg, 91%) was isolated as a beige solid and used without further purification. $^1$H NMR (400 MHz, CDCl$_3$) δ 1.10 (6H,s), 2.42 (2H,s), 2.51 (2H,s), 6.83 (1H,s), 7.42 (1H,dd, J=7.9 and 0.9Hz), 7.64 (1H,dd, J=7.7 and 1.1 Hz), 7.78 (1H,dd, J=7.9 and 1.5 Hz), 7.85 (1H,dd, J=7.7 and 1.4 Hz). MS (ES$^+$) 343/345 (M+1).

Step 2: 1-(2-Cyanophenyl)-6,6-dimethyl-3-(thiazol-2-yl)-4,5,6,7-tetrahydroindol-4-one In the same way as described in Example 15, Step 4 using 3-bromo-1-(2-cyanophenyl)-6,6-dimethyl-4,5,6,7-tetrahydroindol-4-one and 2-tributylstannylthiazole, the title compound (200 mg, 44%) was isolated as a colourless solid. $^1$H NMR (400 MHz, $d_6$-DMSO) δ 1.05 (6H,s), 2.43 (2H,s), 2.53 (2H,s), 7.63 (1H,d, J=3.3 Hz), 7.75–7.80 (4H,m), 7.92 (1H,dd, J=7.8 and 1.4 Hz), 8.13 (1H,dd, J=7.7 and 1.3 Hz). MS (ES$^+$) 348 (M+1).

What is claimed is:

1. A compound of formula (I) or a pharmaceutically acceptable salt thereof:

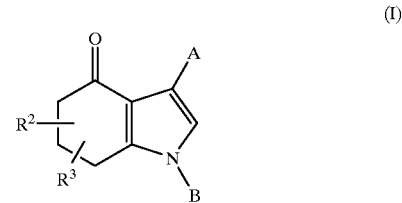

(I)

where A is $C_{1-6}$alkyl, $C_{2-6}$alkenyl, $C_{2-6}$alkynyl, $C_{3-6}$cycloalkyl, aryl$C_{1-6}$alkyl, or aryl wherein the aryl group is optionally substituted by halogen, $C_{1-6}$alkyl, CF$_3$, CN, NO$_2$ or NH$_2$, NR$^1$R$^{10}$, S(O)$_p$R$^1$, heteroaryl$C_{1-6}$alkyl or heteroaryl where heteroaryl is a 5- or 6-membered heteroaromatic ring as defined for B below:

B is phenyl or a 5-membered ring having one or two unsaturations containing 1, 2, 3 or 4 heteroatoms chosen from O, N and S provided that not more than one heteroatom is other than N, a 6-membered heteroaromatic ring containing 1, 2, 3 or 4 nitrogen atoms, each of which rings is optionally substituted by one or more substituents independently chosen from:

cyano;
$C_{1-6}$alkyl;
$C_{1-6}$haloalkyl;
halogen;
S(O)$_p$R$^4$;
COR$^5$;
aryl;
aryl$C_{1-6}$alkyl; or
a 5-membered ring substituent having one or two unsaturations containing 1, 2, 3 or 4 heteroatoms chosen from O, N and S provided that not more than one heteroatom is other than N;
wherein the aryl ring substituent or 5-membered ring substituent is optionally substituted by one, two or three further substituents independently chosen from halogen, CF$_3$, OCH$_3$, nitro and cyano; and when a nitrogen ring atom is present it is optionally substituted by oxygen;

R$^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{1-6}$alkynyl;

$R^2$ and $R^3$ are independently hydrogen or $C_{1-6}$alkyl or together with the carbon atom to which they are attached form a $C_{3-8}$cycloalkyl group;

$R^4$ is hydrogen, $C_{1-8}$alkyl, $C_{2-8}$alkenyl, $C_{2-8}$alkynyl, aryl or $CH_2(CO)_mNR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{10}$ is hydrogen or $C_{1-6}$alkyl;

$R^{14}$ is hydrogen or $C_{1-6}$alkyl;

m is zero or 1;

p is zero, 1 or 2;

q is 1 or 2;

r is 0, 1 or 2;

s is 0, 1 or 2; and t is 0, 1 or 2.

2. A compound according to claim 1 wherein B is phenyl or 6-membered heteroaromatic ring optionally substituted with one or two substituent groups independently chosen from halogen, $C_{1-6}$alkyl, trifluoromethyl, cyano or unsubstituted 5-membered heteroaromatic ring substituent containing 1, 2, 3 or 4 heteroatoms chosen from O, N and S in which not more than one heteroatom is other than N.

3. A composition according to claim 1 wherein A is $C_{1-6}$alkyl, $C_{2-6}$alkenyl, aryl $C_{1-6}$alkyl or aryl wherein the aryl group is optionally substituted by a halogen atom or a $C_{1-6}$alkyl group, a 5- or 6-membered heteroaromatic ring optionally substituted by a halogen atom or $C_{1-6}$alkyl, $NHR^1$ or $SR^1$.

4. A composition according to claim 1, wherein $R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenol or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio.

5. A compound according to claim 1 wherein $R^2$ and $R^3$ are independently chosen from hydrogen and methyl.

6. A pharmaceutical composition comprising a compound according to claim 1, or a pharmaceutically acceptable salt thereof, and a pharmaceutically acceptable excipient.

7. A compound as defined in any one of claims 1 to 5 or a pharmaceutically acceptable salt thereof, with the exception of 6,7-dihydro-3-methyl-1-phenylindol-4(5H)-one and 1,5,6,7-tetrahydro-3,6,6-trimethyl-1-phenylindol-4-one.

* * * * *